US012784148B2

(12) United States Patent
Hong et al.

(10) Patent No.: US 12,784,148 B2
(45) Date of Patent: Nov. 3, 2026

(54) METHOD FOR STANDARDIZING MEDICAL IMAGES AND DEVICE FOR USING THE SAME

(71) Applicant: ONTACT HEALTH CO., LTD., Seoul (KR)

(72) Inventors: Young Taek Hong, Seoul (KR); Ji Na Lee, Seoul (KR); Seung Ah Lee, Seoul (KR); Hack Joon Shim, Seoul (KR); Annes Choi, Seoul (KR)

(73) Assignee: ONTACT HEALTH CO., LTD., Seoul (KR)

( * ) Notice: Subject to any disclaimer, the term of this patent is extended or adjusted under 35 U.S.C. 154(b) by 82 days.

(21) Appl. No.: 18/912,570

(22) Filed: Oct. 10, 2024

(65) Prior Publication Data

US 2025/0131536 A1 Apr. 24, 2025

(30) Foreign Application Priority Data

Oct. 5, 2023 (KR) ........................ 10-2023-0132743
Oct. 4, 2024 (KR) ........................ 10-2024-0135141

(51) Int. Cl.
*G06T 5/60* (2024.01)
*G06T 5/20* (2006.01)
(Continued)

(52) U.S. Cl.
CPC .................. *G06T 5/60* (2024.01); *G06T 5/20* (2013.01); *G06T 5/70* (2024.01); *G06T 7/0012* (2013.01);
(Continued)

(58) Field of Classification Search
None
See application file for complete search history.

(56) References Cited

U.S. PATENT DOCUMENTS 12,524,504 B2 * 1/2026 Muehlberg .......... G06F 18/2193
2022/0101070 A1 * 3/2022 Muehlberg .......... G06F 18/2433
(Continued)

FOREIGN PATENT DOCUMENTS

KR 10-2722318 B1 10/2024

OTHER PUBLICATIONS

S. Woo et al., "ConvNext V2: Co-designing and Scaling ConvNets with Masked Autoencoders," 2023 IEEE/CVF Conference on Computer Vision and Pattern Recognition (CVPR), Vancouver, BC, Canada, 2023, pp. 16133-16142, doi: 10.1109/CVPR52729.2023.01548. (Year: 2023).*
(Continued)

*Primary Examiner* — Tahmina N Ansari
(74) *Attorney, Agent, or Firm* — INVENSTONE PATENT, LLC

(57) ABSTRACT

According to the present disclosure, provided are a method for harmonizing a medical image which includes receiving a medical image for an object, and harmonizing the received medical image to acquire a filtered medical image by using a convolutional filter based on a predictive model trained to output a reconstructed image using the medical image as input, in which the convolutional filter corresponds to a first convolutional layer of the predictive model, and a device using the same and the present disclosure is a technology developed through the Seoul Business Agency of the Seoul Metropolitan Government (2023 Bio-Medical Technology Commercialization Support Project BT230080 Validation of Safety and Efficacy of Echocardiographic Imaging Diagnosis Solution through Myocardial Texture Analysis Based on Ultrasound Imaging).

17 Claims, 15 Drawing Sheets

(51) Int. Cl.

| | |
|---|---|
| ***G06T 5/70*** | (2024.01) |
| ***G06T 7/00*** | (2017.01) |
| ***G06V 10/25*** | (2022.01) |
| ***G06V 10/30*** | (2022.01) |
| ***G06V 10/40*** | (2022.01) |
| ***G06V 10/77*** | (2022.01) |
| ***G06V 10/82*** | (2022.01) |
| ***G16H 30/40*** | (2018.01) |
| ***G16H 50/20*** | (2018.01) |

(52) U.S. Cl.
CPC .............. *G06V 10/25* (2022.01); *G06V 10/30* (2022.01); *G06V 10/40* (2022.01); *G06V 10/7715* (2022.01); *G06V 10/82* (2022.01); *G16H 30/40* (2018.01); *G16H 50/20* (2018.01); *G06T 2207/10068* (2013.01); *G06T 2207/10081* (2013.01); *G06T 2207/10088* (2013.01); *G06T 2207/10116* (2013.01); *G06T 2207/10132* (2013.01); *G06T 2207/20081* (2013.01); *G06T 2207/20084* (2013.01); *G06T 2207/30048* (2013.01); *G06V 2201/03* (2022.01)

(56) References Cited

U.S. PATENT DOCUMENTS

| | | | | |
|---|---|---|---|---|
| 2023/0267604 | A1* | 8/2023 | Dhaouadi | G06T 7/0012 382/131 |
| 2024/0248964 | A1* | 7/2024 | Muehlberg | G06F 18/2193 |
| 2025/0131536 | A1* | 4/2025 | Hong | G06V 10/30 |

OTHER PUBLICATIONS

"DeepHarmony: A deep learning approach to contrast harmonization across scanner changes" Magnetic resonance imaging 64 (2019): 160-170(Jul. 10, 2019).

Silvia Seoni et al. "All you need is data preparation: A systematic review of image harmonization techniques in Multi-center/device studies for medical support systems." Computer Methods and Programs in Biomedicine 2024; (Available online Apr. 23, 2024).

Soolmaz Abbasi et al. "Deep learning for the harmonization of structural MRI scans: a survey." BioMedical Engineering OnLine 23.1 (2024): 90.; (Published onlline: Aug. 31, 2024).

Sanghyun Woo et al. "Convnext v2: Co-designing and scaling convnets with masked autoencoders." Proceedings of the IEEE/CVF Conference on Computer Vision and Pattern Recognition. 2023.

Mohd Usama et al. "A Domain Adaptation Model for Carotid Ultrasound: Image Harmonization, Noise Reduction, and Impact on Cardiovascular Risk Markers." arXiv preprint arXiv:2407.05163 (2024); (Available online Apr. 3, 2025).

Elisavet Stamoulou et al. "Harmonization Strategies in Multicenter MRI-Based Radiomics", J. Imaging 2022, 8, 303.

Self-Supervised Convolutional Kernel-Based Handcrafted Feature Harmonization: Enhanced Left Ventricle Hypertension Disease Phenotyping on Echocardiography, arXiv:2310.08897v3 [eess.IV] Nov. 22, 2023.

* cited by examiner

ORIGINAL

PREDICTIVE MODEL OF PRESENT DISCLOSURE (COLOR)

PREDICTIVE MODEL OF PRESENT DISCLOSURE (ULTRASOUND)

| | Mean ± SD | Median |
|---|---|---|
| Original | 0.0393 ± 0.0755 | 0.0228 |
| Combat | 0.0330 ± 0.0483 | 0.0245 |
| PREDICTIVE MODEL OF PRESENT DISCLOSURE (COLOR) | 0.0740 ± 0.1023 | 0.0305 |
| PREDICTIVE MODEL OF PRESENT DISCLOSURE (ULTRASOUND) | 0.0284 ± 0.0347 | 0.0204 |

FIG. 6B

| | Accuracy | AUC | Sensitivity | Specificity | F1-Score |
|---|---|---|---|---|---|
| Original | 0.58 ± 0.07 [0.54, 0.63] | 0.54 ± 0.07 [0.50, 0.58] | 0.53 ± 0.21 [0.40, 0.66] | 0.68 ± 0.23 [0.54, 0.83] | 0.60 ± 0.13 [0.51, 0.68] |
| Combat | 0.61 ± 0.08 [0.56, 0.66] | 0.57 ± 0.06 [0.53, 0.61] | 0.53 ± 0.23 [0.39, 0.68] | 0.75 ± 0.20 [0.63, 0.87] | 0.61 ± 0.16 [0.51, 0.71] |
| PREDICTIVE MODEL OF PRESENT DISCLOSURE (COLOR) | 0.83 ± 0.07 [0.79, 0.87] | 0.86 ± 0.07 [0.82, 0.90] | 0.83 ± 0.08 [0.78, 0.88] | 0.84 ± 0.09 [0.79, 0.90] | 0.86 ± 0.06 [0.63, 0.90] |
| PREDICTIVE MODEL OF PRESENT DISCLOSURE (ULTRASOUND) | 0.85 ± 0.12 [0.77, 0.92] | 0.83 ± 0.17 [0.73, 0.94] | 0.89 ± 0.09 [0.84, 0.95] | 0.77 ± 0.22 [0.82, 0.90] | 0.88 ± 0.09 [0.83, 0.94] |

FIG. 7B

| | Mean ± SD | Median |
|---|---|---|
| Original | 0.0577 ± 0.0622 | 0.0426 |
| Combat | 0.0509 ± 0.0336 | 0.0378 |
| PREDICTIVE MODEL OF PRESENT DISCLOSURE (COLOR) | 0.0478 ± 0.0578 | 0.0380 |
| PREDICTIVE MODEL OF PRESENT DISCLOSURE (ULTRASOUND) | 0.0460 ± 0.0609 | 0.0332 |

FIG. 8B

METHOD FOR STANDARDIZING MEDICAL IMAGES AND DEVICE FOR USING THE SAME

CROSS-REFERENCE TO RELATED APPLICATIONS

This application claims the priority of Korean Patent Application No. 10-2023-0132743 filed on Oct. 5, 2023, and Korean Patent Application No. 10-2024-0135141 filed on Oct. 4, 2024 in the Korean Intellectual Property Office, the disclosure of which is incorporated herein by reference.

BACKGROUND

Field

The present disclosure relates to a method for harmonizing medical images and a device for harmonizing medical images using the same.

Description of the Related Art

Recently, with the development of artificial intelligence and machine learning technology, the method of extracting important information from medical images is changing innovatively. In particular, a method for quantitatively analyzing medical image data is receiving attention, and these features are expressed by various statistical values (e.g., mean, median, variance, etc.) and play an important role in classifying diseases.

In this case, reproducibility of handcrafted features may be an important factor that directly affects the ability of a model to accurately predict prognosis.

Meanwhile, handcrafted features may be damaged due to pixel intensity variations caused by characteristics, protocols, or settings of imaging technology, and may be difficult to guarantee consistent performance of a model, especially when image acquisition conditions change.

In particular, when image acquisition methods and parameters are different depending on each hospital or device manufacturer, the reproducibility of the image features may deteriorate, which may lower the reliability of analysis results.

The need for image harmonization technology to solve this problem is emerging. In particular, in the case of ultrasound images, since there is variability in the analysis results due to various device manufacturers and differences in settings, a robust harmonization technology to solve this problem is required.

The technology that forms the background of the invention has been written to facilitate a better understanding of the present disclosure. It should not be understood that the matters described in the technology that form the background of the invention exist as the related art.

The present disclosure is a technology developed through the Seoul Business Agency of the Seoul Metropolitan Government (2023 Bio-Medical Technology Commercialization Support Project BT230080 Validation of Safety and Efficacy of Echocardiographic Imaging Diagnosis Solution through Myocardial Texture Analysis Based on Ultrasound Imaging).

SUMMARY

Meanwhile, a statistical harmonization technique has been proposed as a solution to solve the above-described problem. The statistical harmonization technique focuses on fitting a distribution of each data by applying an empirical Bayes method to remove a batch effect that occurs in multi-institution or multi-manufacturer dataset.

In this case, the statistical harmonization method integrates the feature distribution by adjusting the mean, variance, covariance, etc., of original data, but may be difficult to solve a nonlinear difference between data.

In other words, the conventional statistical harmonization techniques still fail to solve the problem that the features (especially, handcrafted features) in the image appear inconsistently because the image acquisition methods and parameter settings are different for each manufacturer.

Meanwhile, the inventors of the present disclosure have focused on an artificial neural network-based convolutional filter.

More specifically, the inventors of the present disclosure introduced a convolutional filter of an artificial neural network based on self-supervised learning to develop a convolutional filter that can train medical image data even in a state without a label to extract consistent features regardless of manufacturers or parameter settings.

In other words, the inventors of the present disclosure may process large-scale medical image data through the convolutional filter and go through a filtering process of harmonizing differences between each manufacturer to improve the quality of images and extract consistent imaging features, which could be expected to enhance classification accuracy of diseases.

In particular, the inventors of the present disclosure could expect that the reliability and reproducibility of handcrafted features may be supported through the harmonization of the medical images using the convolutional filter.

As a result, the inventors of the present disclosure developed a new harmonization system for medical images based on the convolutional filter.

In this case, the inventors of the present disclosure attempted to apply a filter based on an artificial neural network model to the new harmonization system for medical images, with the filter having the ability to train and express unique features (or representative features) that appear only in specific medical images, such as cardiac ultrasound images.

The inventors of the present disclosure could expect that, by providing a new system for harmonizing medical images, it is possible to provide highly reliable analysis results for medical images such as cardiac ultrasound images.

Therefore, an object to be achieved by the present disclosure is to provide a method for harmonizing medical images including receiving a medical image for an object and harmonizing the medical image using a convolutional filter based on a predictive model, and a device using the same.

Aspects of the present disclosure are not limited to the above-mentioned aspects. That is, other aspects that are not mentioned may be obviously understood by those skilled in the art from the following specification.

In order to solve the above-described problem, a method for harmonizing medical images according to an exemplary embodiment of the present disclosure is provided.

The method includes receiving a medical image for an object, and harmonizing the received medical image to acquire a filtered medical image by using a convolutional filter based on a predictive model trained to output a reconstructed image using the medical image as input, in which the convolutional filter corresponds to a first convolutional layer of the predictive model.

According to a feature of the present disclosure, the method may further include generating a mask for a region of interest (ROI) in the filtered medical image, and extracting features based on the region of interest or the mask.

According to another feature of the present disclosure, the extracting of the features may include overlaying the mask on the filtered medical image to acquire an overlaid medical image and extracting features for the overlaid medical image.

According to still another feature of the present disclosure, the extracting of the features may include performing discretization of a grayscale based on pixel intensity of the region of interest, and extracting radiomics features and statistical features for the region of interest based on the discretization result.

According to still another feature of the present disclosure, the extracting of the features may include extracting handcrafted feature of at least one of morphological features, texture features, and pixel histogram-based features based on the region of interest or the mask.

According to still another feature of the present disclosure, the method may further include, after the extracting of the features, predicting whether a target disease occurs based on the features.

According to still another feature of the present disclosure, the predictive model may be an artificial neural network model based on a masked autoencoder configured to perform self-supervised learning of unique features of the medical image.

According to still another feature of the present disclosure, the first convolutional layer may be configured to perform a filtering function of reducing noise of the input medical image by training a feature map divided into patch units for the input medical image.

According to still another feature of the present disclosure, the medical image may be at least one of an ultrasound image, an X-ray image, a computed tomography (CT) image, a magnetic resonance imaging (MRI) image, and an endoscopic image.

According to still another feature of the present disclosure, the medical image may be a cardiac ultrasound image.

To solve the above-described problem, a device for harmonizing medical images according to another exemplary embodiment of the present disclosure is provided. The device includes a communication unit configured to receive a medical image for an object, and a processor functionally connected to the communication unit, in which the processor is configured to perform harmonization on the received medical image to acquire a filtered medical image by using a convolutional filter based on a predictive model trained to output a reconstructed image using the medical image as input, and the convolutional filter corresponds to a first convolution layer of the predictive model.

According to a feature of the present disclosure, the processor may be further configured to generate a mask for a region of interest in the filtered medical image and extract features based on the region of interest or the mask.

According to another feature of the present disclosure, the processor may be further configured to overlay the mask on the filtered medical image to acquire an overlaid medical image and extract features for the overlaid medical image.

According to a feature of the present disclosure, the processor may be further configured to perform discretization of a grayscale based on pixel intensity of the region of interest and extract radiomics features and statistical features for the region of interest based on the discretization result.

According to another feature of the present disclosure, the processor may be further configured to extract handcrafted feature of at least one of morphological features, texture features, and pixel histogram-based features based on the region of interest or the mask.

According to still another feature of the present disclosure, the processor may be further configured to predict whether a target disease occurs based on the features.

Detailed contents of other exemplary embodiments are described in a detailed description and are illustrated in the drawings.

The present disclosure provides a new system for harmonizing medical images to increase the consistency of data through standardization and harmonization of various medical image data. In particular, the present disclosure may establish a standard for applying the same analysis and diagnosis criteria by reducing a deviation between medical images collected from different manufacturers or capturing environments.

As a result, according to the present disclosure, it is possible to minimize statistical differences between data and derive highly reliable results in clinical diagnosis and research.

In particular, according to the present disclosure, it is possible to support the reliability and reproducibility of handcrafted features through harmonization of medical images through a convolutional filter.

According to the present disclosure, by applying an artificial neural network-based convolutional filter based on image features to train a correlation between the respective pixels, it is possible to reduce noise or distortion in images and generate standardized images while maintaining clinically important information.

In other words, unlike the existing methods, the medical image data harmonized by the new system for harmonizing medical images can support more quantitative and objective diagnosis, and can also improve the learning performance of the artificial intelligence model.

As a result, according to the present disclosure, it is possible to improve the quality of medical images, further increase the accuracy of image-based diagnosis and furthermore greatly increase the efficiency of multi-institution and large-scale data analysis.

The effects according to the present disclosure are not limited to the contents exemplified above, and further various effects are included in the present specification.

The effects of the present disclosure are not limited to the aforementioned effects, and other effects, which are not mentioned above, will be apparently understood to a person having ordinary skill in the art from the following description.

The objects to be achieved by the present disclosure, the means for achieving the objects, and the effects of the present disclosure described above do not specify essential features of the claims, and, thus, the scope of the claims is not limited to the disclosure of the present disclosure.

BRIEF DESCRIPTION OF DRAWINGS

The above and other aspects, features and other advantages of the present disclosure will be more clearly understood from the following detailed description taken in conjunction with the accompanying drawings, in which:

FIGS. 5A and 5B, 6A and 6B, 7A and 7B, and 8A and 8B are diagrams illustrating evaluation results of a predictive model used in an information providing method according to various exemplary embodiments of the present disclosure.

DETAILED DESCRIPTION OF THE EMBODIMENT

Figure 1:
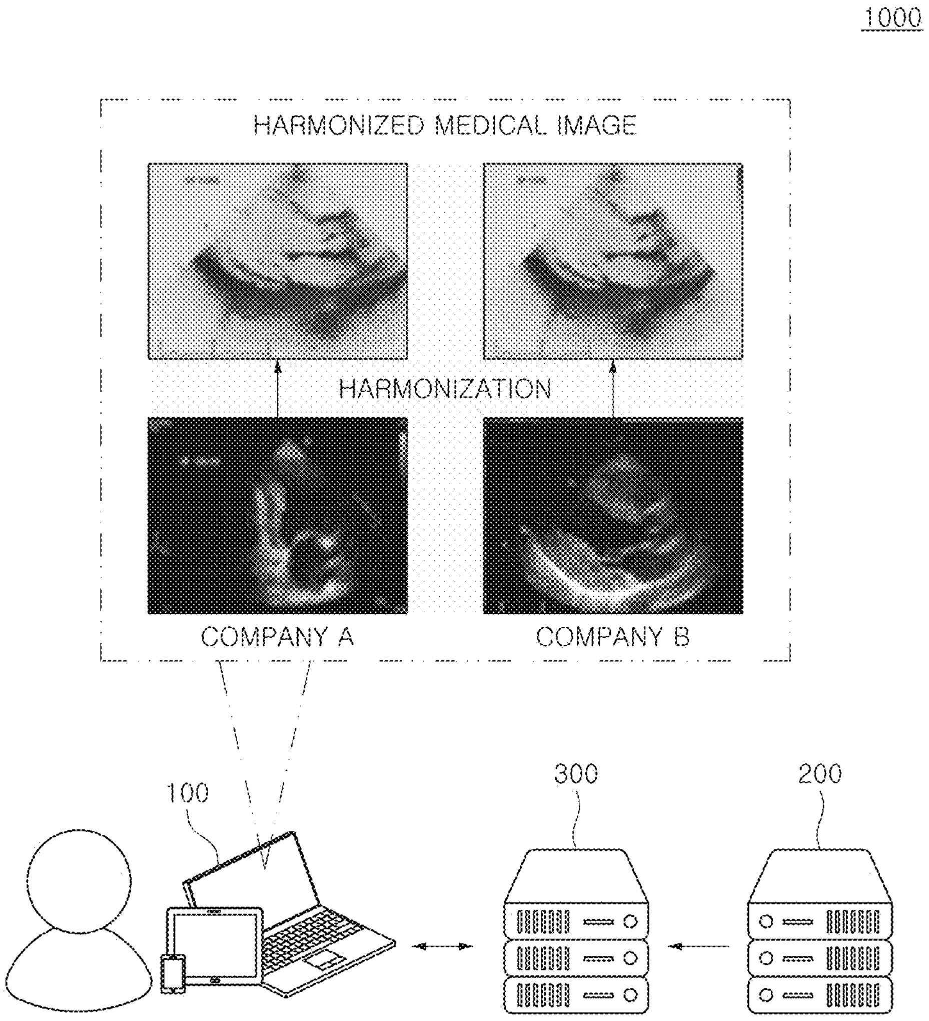
FIG. 1 illustrates a system for harmonizing medical images using a device for harmonizing medical images according to an exemplary embodiment of the present disclosure.

Various advantages and features of the present disclosure and methods accomplishing them will become apparent from the following description of exemplary embodiments with reference to the accompanying drawings. However, the present disclosure is not limited to exemplary embodiments disclosed below, and may be implemented in various different forms, these exemplary embodiments will be provided only in order to make the present disclosure complete and allow one of ordinary skill in the art to which the present disclosure pertains to completely recognize the scope of the present disclosure.

The shapes, sizes, proportions, angles, numbers, etc., disclosed in the drawings for describing exemplary embodiments of the present disclosure are illustrative, and the present disclosure is not limited to the matters illustrated. Further, when it is determined that the detailed description of the known art related to the present disclosure may obscure the gist of the present disclosure, the detailed description thereof will be omitted. When "includes", "having", "formed of", etc., described in the present specification are used, other parts may be added unless "only" is used. When a component is expressed in the singular, it may include a case in which the plural is included unless otherwise explicitly stated.

When interpreting components, it is interpreted to include an error range even if there is no separate explicit statement.

Each feature of various exemplary embodiments of the present disclosure may be partially or fully coupled or combined with each other, and as can be fully understood by those skilled in the art, various technical linkages and operations are possible, and each exemplary embodiment can be implemented independently of each other and can be performed together due to the related relationship.

For clarity in the interpretation of the present specification, the terms used in the present specification will be defined below.

The term "medical image" used in the present specification is a concept that includes ultrasound images, X-ray images, computed tomography (CT) images, magnetic resonance imaging (MRI) images, endoscopic images, etc., and may mean all forms of image data captured to visually represent an anatomical structure or a pathological condition of an object.

In various exemplary embodiments of the present disclosure, the medical image may be an ultrasound image, preferably a cardiac ultrasound image, but is not limited thereto.

For example, the medical image may be a cardiac ultrasound image of an object, which may be a still cut image of a single frame or a video composed of multiple frames. In this case, the cardiac ultrasound image may be a 2D or 3D image.

The term "standardization of medical images," "harmonization of medical images," or "unity of medical images" used in the present specification may refer to a process of reducing variability between medical images caused by different capturing environments, devices, or protocols, and converting data into a consistent form according to specific criteria to increase the reliability and reproducibility of analysis.

The term "convolutional filter" used in the present specification may refer to an artificial neural network-based filter used to emphasize features such as specific patterns, boundaries, and textures in an input medical image or to reduce noise.

That is, it may be possible to acquire a harmonized medical image through the convolutional filter.

Accordingly, in the present specification, the "harmonized medical image" may be used interchangeably with the "filtered medical image."

In various exemplary embodiments of the present disclosure, the convolutional filter may correspond to the first convolutional layer of the predictive model.

The term "first convolutional layer" used in the present specification refers to the first layer of the convolutional network that performs initial filtering and feature learning on the input medical image of the predictive model.

In various exemplary embodiments of the present disclosure, the first convolutional layer may serve to extract important features of the image through filtering based on patches of the input medical image and simultaneously reduce noise.

The term "predictive model" used in the present specification refers to an artificial neural network model trained to achieve a specific purpose (e.g., image reconstruction, feature extraction, disease prediction, etc.) from an input medical image, and may be a model including a 2D convolutional kernel that serves as a filter, specifically to detect specific patterns or features in 2D image data and generate a feature map based on the detected specific patterns and features.

In this case, the predictive model may be a model based on self-supervised learning.

The term "self-supervised learning" used in the present specification refers to a machine learning technique that automatically trains meaningful features by training patterns, structural characteristics, or latent representations of data based on data without a label.

In various exemplary embodiments of the present disclosure, the predictive model may be a model based on a masked autoencoder. For example, the predictive model may be an image processing model of ConvNeXt-V2, but is not limited thereto, and various image processing models may be adopted as the predictive model according to various exemplary embodiments of the present disclosure.

For example, at least one algorithm among ResNet-50, ResNet-101, ResNet-152, DenseNet-121, DenseNet-169, DenseNet-201, VGG-16, VGG-19, GoogLeNet, Inception-V3, Inception-ResNet, UNet, Attention UNet, and ResUNet may be selected as the predictive model according to various exemplary embodiments of the present disclosure.

The term "region of interest (ROI)" used in the present specification refers to a region including a specific anatomical structure or lesion in medical images, and in the present disclosure, may refer to a specific part defined by generating a mask. For example, in a cardiac ultrasound image, left ventricle or myocardium may be the ROI.

The term "mask" used in the present specification is a binary form generated to emphasize a boundary or specific part of the ROI, and may clearly distinguish the ROI and focus on the specific region for analysis.

The term "handcrafted features" used in the present specification are features defined manually based on the knowledge of a domain expert, and may be used to quantitatively express a specific pattern of an image or a shape of a lesion.

In various exemplary embodiments of the present disclosure, the handcrafted features include morphological features, texture features, and histogram-based features.

In this case, the morphological features are indicators that quantitatively represent the form or shape of the specific structure in the medical images, and include features such as the size, shape, circumference length, circularity, and asymmetry of the ROI. For example, the morphological features may include a ratio of length and width of the lesion, an area, complexity of the boundary, etc.

The texture features are features that measure the relationship between pixel intensities or repeatability of patterns in an image, and may be features that mainly quantitatively represent texture of an image, arrangement of pixels, and irregularity of pixels. For example, the texture features may include entropy, energy, contrast, homogeneity, etc.

The histogram-based features are indicators that represent the distribution of pixel values in an image, and may include mean, median, variance and percentile of the pixel values, and frequency of occurrence of specific intensity values, etc., which may be used to quantify and analyze the overall brightness and contrast of an image.

However, the types of handcrafted features are not limited to those described above.

The term "discretization of grayscales" used in the present specification may refer to a process of dividing a range of pixel values of a medical image into certain bins to quantitatively express the change in pixel intensity.

According to the features of the present disclosure, before extracting radiomic features within the ROI, the discretization may be performed, and thus, the characteristics of data may be normalized.

The term "radiomic features" used in the present specification refers to features that numerically express statistical distributions, patterns, textures, shapes, etc., of pixel values in medical images.

In this case, the radiomic features may include first-order statistical features, gray-level co-occurrence matrices (GLCM), gray-level run-length matrices (GLRLM), gray-level size zone matrices (GLSZM), gray-level dependence matrices (GLDM), and neighboring gray-tone difference matrices (NGTDM), etc.

The term "target disease" used in the present specification refers to a specific disease state to be predicted or classified, and in the present disclosure, may include heart disease, cancer lesions, nervous system diseases, etc. For example, left ventricular hypertrophy, myocardial stiffness, myocardial ischemia, etc., based on cardiac ultrasound images may be target diseases.

In this case, the classification of the target disease may be performed by a classification model based on the harmonized medical images.

For example, the classification of the target disease may be performed by a classification model trained to classify whether a disease has occurred by inputting the harmonized medical image.

Hereinafter, a system for harmonizing medical images using a device for harmonizing medical images and the device for harmonizing medical images according to an exemplary embodiment of the present disclosure will be described with reference to FIGS. 1 and 2A and 2B.

FIG. 1 illustrates a system for harmonizing medical images using a device for harmonizing medical images according to an exemplary embodiment of the present disclosure. FIG. 2A illustrates an exemplary configuration of a user device that receives a harmonized medical image according to an exemplary embodiment of the present disclosure. FIG. 2B illustrates an exemplary configuration of a server for harmonizing medical images according to an exemplary embodiment of the present disclosure.

First, referring to FIG. 1, a system 1000 for harmonizing medical images may be a system configured to provide harmonized medical images based on medical images of an object. In this case, the system 1000 for harmonizing medical images may be configured to include a user device 100 for receiving harmonized medical images, a medical image providing server 200 for providing or storing various medical image DBs such as ultrasound images, and a harmonization server 300 for generating harmonized medical images based on the received medical images.

In various exemplary embodiments of the present disclosure, the harmonization server 300 may be mounted on an image diagnosis device (not illustrated). In this case, various types of information related to measurement values may be displayed on a display unit of the image diagnosis device (not illustrated).

That is, a user may check a harmonized medical image at the same time as the diagnosis through the image diagnosis device.

In various exemplary embodiments, the user device 100 is an electronic device that provides a user interface for displaying the harmonized medical image, and may include at least one of a smartphone, a tablet personal computer (PC), a laptop, and/or a PC.

The user device 100 may receive the harmonized medical image from the harmonization server 300 and display the received result through the display unit (not illustrated).

The harmonization server 300 may include a general-purpose computer, a laptop, and/or a data server, etc., that perform various calculations for providing the harmonized medical image based on the medical image provided from the medical image providing server 200. In this case, the harmonization server 300 may be a device for accessing a web server providing a web page or a mobile web server providing a mobile website, but is not limited thereto.

More specifically, the harmonization server 300 receives a medical image from the medical image providing server 200 and performs convolutional filter-based harmonization on the received medical image.

In this way, the image provided from the harmonization server 300 may be provided as a web page through a web browser installed on the user device 100, or may be provided in the form of an application or program. In various exemplary embodiments, such data may be provided in a form included in a platform in a client-server environment.

Next, the components of the harmonization server 300 of the present disclosure will be specifically described with reference to FIGS. 2A and 2B.

Figure 2A:
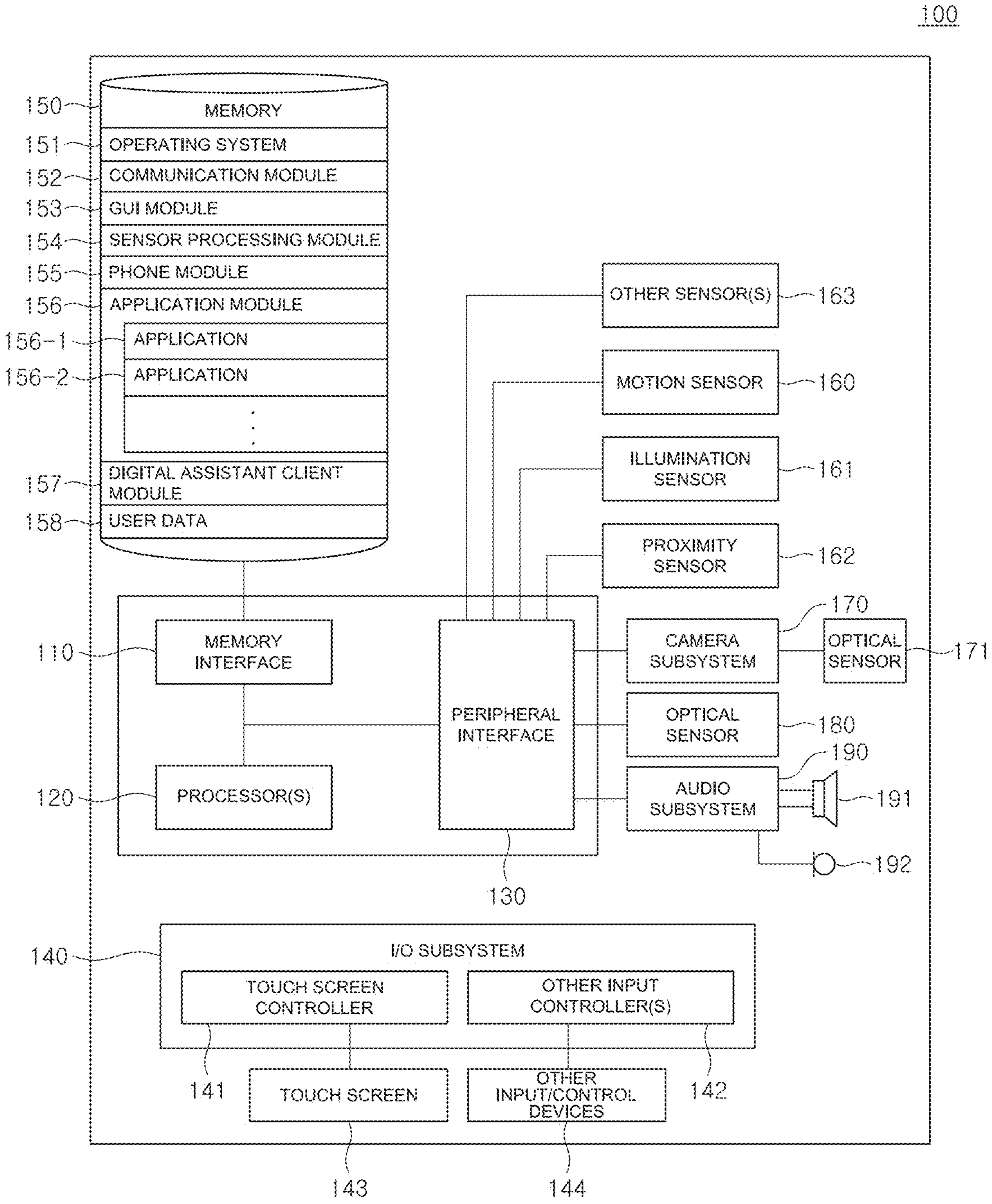
FIG. 2A is a block diagram illustrating a configuration of a user device according to an exemplary embodiment of the present disclosure.

Referring to FIG. 2A, the user device 100 may include a memory interface 110, one or more processors 120, and a peripheral interface 130. Various components in the user device 100 may be connected by one or more communication buses or signal lines.

The memory interface 110 may be connected to a memory 150 to transmit various data to the processor 120. Here, the memory 150 may include at least one type of storage media such as flash memory type, hard disk type, multimedia card micro type, card type memory (for example, SD or XD memory, etc.), RAM, SRAM, ROM, EEPROM, PROM, network storage, cloud, and blockchain data.

In various exemplary embodiments, the memory 150 may store at least one of an operating system 151, a communication module 152, a graphical user interface (GUI) module 153, a sensor processing module 154, a telephone module 155, and an application module 156. Specifically, the operating system 151 may include instructions for processing basic system services and instructions for performing hardware operations. The communication module 152 may communicate with at least one of other devices, computers, and servers. The graphical user interface (GUI) module 153 may process a graphical user interface. The sensor processing module 154 may process sensor-related functions (e.g., processing voice input received using one or more microphones 192). The telephone module 155 may process a telephone-related function. The application module 156 may perform various functions of a user application, such as electronic messaging, web browsing, media processing, navigation, imaging, and other processing functions. In addition, the user device 100 may store one or more software applications 156-1 and 156-2 (e.g., information providing applications) associated with a type of service in the memory 150.

In various exemplary embodiments, the memory 150 may store a digital assistant client module 157 (hereinafter, DA client module), and thus, may store instructions for performing functions of the digital assistant client side and various user data 158.

Meanwhile, the DA client module 157 may acquire voice input, text input, touch input, and/or gesture input of a user through various user interfaces (e.g., I/O subsystem 140) provided in the user device 100.

In addition, the DA client module 157 may output data in an audiovisual or tactile form. For example, the DA client module 157 may output data composed of a combination of at least one of the following: voice, sound, notification, text message, menu, graphic, video, animation, and vibration. In addition, the DA client module 157 may communicate with a digital assistant server (not illustrated) using the communication subsystem 180.

In various exemplary embodiments, the DA client module 157 may collect additional information on the surrounding environment of the user device 100 from various sensors, subsystems, and peripheral devices to construct a context associated with the user input. For example, the DA client module 157 may provide context information along with the user input to a digital assistant server to infer the user's intention. Here, the context information that may accompany the user input may include sensor information, such as lighting, ambient noise, ambient temperature, images of the surrounding environment, and videos. As another example, the context information may include physical states (e.g., device orientation, device position, device temperature, power level, speed, acceleration, motion pattern, cellular signal strength, etc.) of the user device 100. As another example, the context information may include information (e.g., processes running on the user device 100, installed programs, past and present network activity, background services, error logs, resource usage, etc.) related to a software status of the user device 100.

In various exemplary embodiments, the memory 150 may include additional or deleted instructions, and furthermore, the user device 100 may include additional components or exclude some components in addition to the components illustrated in FIG. 2A.

The processor 120 may control the overall operation of the user device 100, and may perform various commands to implement an interface for providing harmonized medical images by running applications or programs stored in the memory 150.

The processor 120 may correspond to a computational device such as a central processing unit (CPU) or an application processor (AP). In addition, the processor 120 may be implemented in the form of an integrated chip (IC) such as a system on chip (SoC) in which various computational devices such as a neural processing unit (NPU) are integrated.

The peripheral interface 130 may be connected to various sensors, subsystems, and peripheral devices to provide data so that the user device 100 may perform various functions. Here, performing any function by the user device 100 may be understood as being performed by the processor 120.

The peripheral interface 130 may receive data from a motion sensor 160, an illumination sensor (light sensor) 161, and a proximity sensor 162, so the user device 100 may perform orientation, light, proximity detection functions, etc. As another example, the peripheral interface 130 may receive data from other sensors 163 (positioning system-GPS receiver, temperature sensor, and biometric sensor), so the user device 100 may perform functions related to the other sensors 163.

In various exemplary embodiments, the user device 100 may include a camera subsystem 170 connected to the peripheral interface 130 and an optical sensor 171 connected thereto, so the user device 100 may perform various capturing functions, such as taking pictures and recording video clips.

In various exemplary embodiments, the user device 100 may include a communication subsystem 180 connected to the peripheral interface 130. The communication subsystem 180 may include one or more wired/wireless networks and may include various communication ports, radio frequency transceivers, and optical transceivers.

In various exemplary embodiments, the user device 100 may include an audio subsystem 190 connected to the peripheral interface 130, and the audio subsystem 190 may include one or more speakers 191 and one or more microphones 192, so that the user device 100 may perform voice-activated functions, such as voice recognition, voice duplication, digital recording, and telephone functions.

In various exemplary embodiments, the user device 100 may include the I/O subsystem 140 connected to the peripheral interface 130. For example, the I/O subsystem 140 may control a touch screen 143 included in the user device 100 via a touch screen controller 141. As an example, the touch screen controller 141 may detect the user's contact and movement or the stop of the user's contact and movement using any one of a plurality of touch sensing technologies, such as a capacitive type, a resistive type, an infrared type, a surface acoustic wave technology, and a proximity sensor array. As another example, the I/O subsystem 140 may control other input/control devices 144 included in the user device 100 via other input controller(s) 142. As an example, the other input controller(s) 142 may control one or more buttons, rocker switches, thumb-wheels, infrared ports, USB ports, and pointer devices, such as a stylus.

Figure 2B:
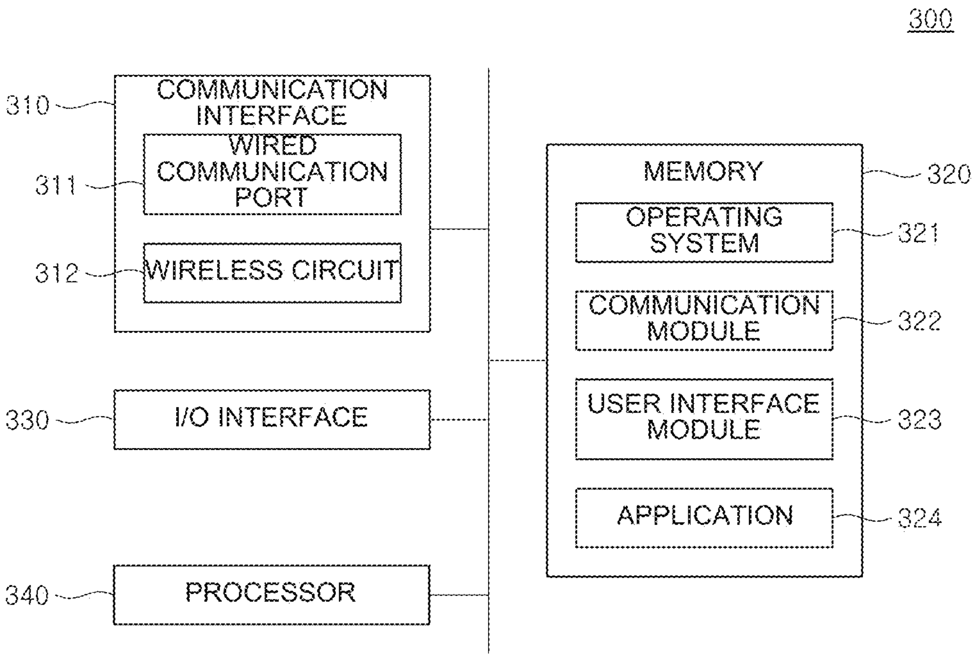
FIG. 2B is a block diagram illustrating a configuration of a server for harmonization according to an exemplary embodiment of the present disclosure.

Next, referring to FIG. 2B, the harmonization server 300 may include a communication interface 310, a memory 320, an I/O interface 313, and a processor 314 and each component may communicate with one another through one or more communication buses or signal lines.

The communication interface 310 may be connected to the user device 100 and the medical image providing server 200 via a wired/wireless communication network to exchange data. For example, the communication interface 310 may receive a medical image from the medical image providing server 200, and generate a harmonized medical image from the received medical image, and transmit the generated harmonized medical image to the user device 100.

Meanwhile, the communication interface 310 that enables the transmission and reception of such data includes a communication port 311 and a wireless circuit 312, and the wired communication port 311 may include one or more wired interfaces, for example, Ethernet, a universal serial bus (USB), FireWire, etc. In addition, the wireless circuit 312 may transmit and receive data with an external device via RF signals or optical signals. In addition, the wireless circuit 312 may use at least one of a plurality of communication standards, protocols, and technologies, such as GSM, EDGE, CDMA, TDMA, Bluetooth, Wi-Fi, VoIP, Wi-MAX, or any other suitable communication protocol.

The memory 320 may store various data used in the harmonization server 300. For example, the memory 320 may store a medical image, or store a convolutional filter trained to provide a harmonized image from the medical image, i.e., a predictive model including the convolutional filter.

In various exemplary embodiments, the memory 320 may include volatile or nonvolatile recording media capable of storing various data, commands, and information. For example, the memory 320 may include at least one type of storage media such as flash memory type, hard disk type, multimedia card micro type, card type memory (e.g., SD or XD memory, etc.), RAM, SRAM, ROM, EEPROM, PROM, network storage, cloud, and blockchain data.

In various exemplary embodiments, the memory 320 may store at least one of an operating system 321, a communication module 322, a user interface module 323, and one or more applications 324.

The operating system 321 (e.g., an embedded operating system such as LINUX, UNIX, MAC OS, WINDOWS, and VxWorks) may include various software components and drivers for controlling and managing general system operations (e.g., memory management, storage device control, power management, etc.) and may support communication between various hardware, firmware, and software components.

The communication module 322 may support communication with other devices via the communication interface 310. The communication module 322 may include various software components for processing data received by the wired communication port 311 or the wireless circuit 312 of the communication interface 310.

The user interface module 323 may receive user request or input from a keyboard, a touch screen, a microphone, etc., via the I/O interface 330, and may provide a user interface on a display.

The application 324 may include a program or module configured to be executed by one or more processors 340. Here, the application for providing the harmonized medical image may be implemented on a server farm.

The I/O interface 330 may connect at least one of input/output devices (not illustrated) of the harmonization server 300, such as a display, a keyboard, a touch screen, and a microphone, to the user interface module 323. The I/O interface 330 may receive the user input (e.g., voice input, keyboard input, touch input, etc.) together with the user interface module 323, and process commands according to the received input.

The processor 340 may be connected to the communication interface 310, the memory 320, and the I/O interface 330 to control the overall operation of the harmonization server 300, and may perform various commands for providing information through an application or program stored in the memory 320.

The processor 340 may correspond to a computational device such as a central processing unit (CPU) or an application processor (AP). In addition, the processor 340 may be implemented in the form of an integrated chip (IC) such as a system on chip (SoC) in which various computational devices are integrated. Alternatively, the processor 340 may include a module for calculating an artificial neural network model such as a neural processing unit (NPU).

In various exemplary embodiments, the processor 340 may be configured to determine the ROI within the medical image using the predictive model and extract the handcrafted features. Furthermore, the processor 340 may be configured to derive clinical results, such as whether a disease occurs and prognosis, based on the handcrafted features. Hereinafter, a method for harmonizing medical images according to an exemplary embodiment of the present disclosure will be described in detail with reference to FIGS. 3A and 3B and 4A and 4B.

FIGS. 3A and 3B and 4A and 4B are diagrams illustrating a procedure of a method for harmonizing medical images according to an exemplary embodiment of the present disclosure.

Figure 3A:
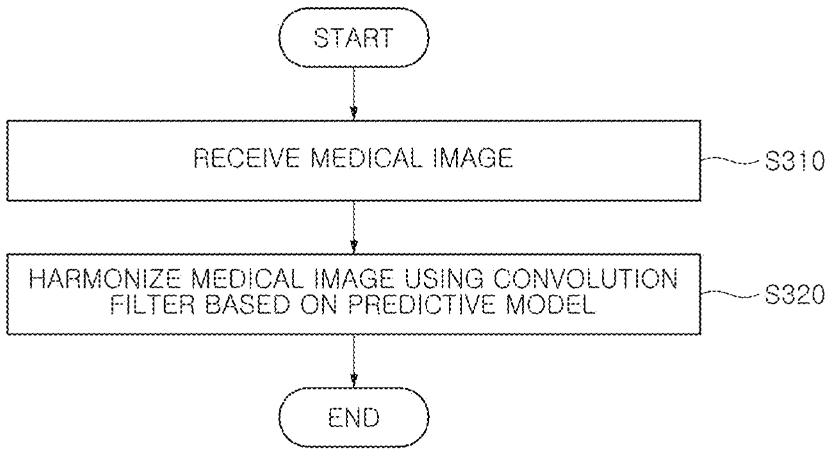
FIGS. 3A and 3B and 4A and 4B are diagrams illustrating a procedure of a method for harmonizing medical images according to an exemplary embodiment of the present disclosure.

First, referring to FIG. 3A, an information providing procedure according to an exemplary embodiment of the present disclosure is as follows. First, a medical image for an object is received (S310). Then, the convolutional filter-based harmonization is performed (S320).

More specifically, in the step of receiving the medical image (S310), a medical image for a target area may be received.

In various exemplary embodiments of the present disclosure, at least one medical image among an ultrasound image, an X-ray image, a CT image, an MRI image, and an endoscopic image may be received.

Next, the harmonization is performed on the received medical image using a convolutional filter based on a predictive model that is trained to output a reconstructed image using a medical image as input (S320).

Figure 3B:
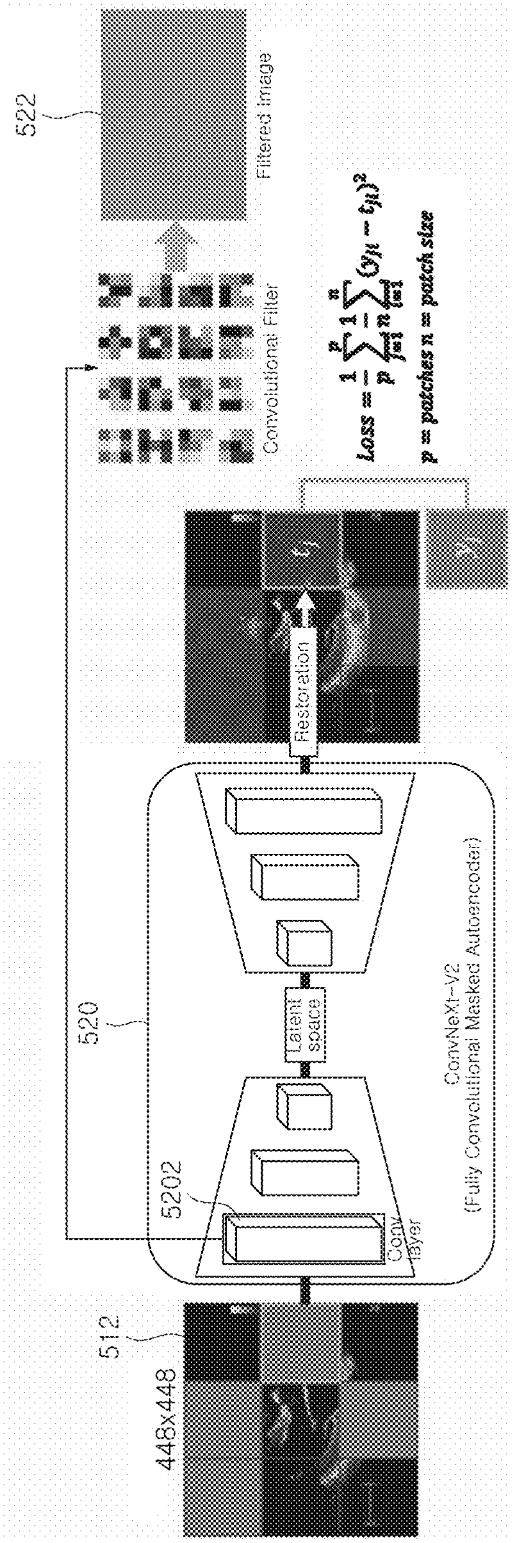

More specifically, referring to FIG. 3B, a medical image 512 of a cardiac ultrasound image is received from the above-described medical image providing server 200 and input to the predictive model 520.

In this case, the predictive model 320 is an artificial neural network model trained to achieve a specific purpose (e.g., image reconstruction, feature extraction, disease prediction, etc.) from the input medical image, and includes a first convolution layer 5202 that performs initial filtering and feature learning on the input medical image of the predictive model.

In this case, the first convolution layer 5202 may correspond to a 2D convolutional kernel that serves as a filter used, especially to detect specific patterns or features in 2D image data and generate a feature map based on the detected specific patterns or features.

That is, a filtered medical image 522 may be acquired by passing through the convolutional filter of the first convolution layer 5202.

In this case, the filtered medical image 522 may be provided as the harmonized medical image that provides clearer visual information in the subsequent analysis and feature extraction process, in the form that the important features of the input original medical image are emphasized, and noise is removed.

The harmonized medical image, the image through the filtering process may contribute to improving reliability and accuracy in medical diagnosis and research by better revealing the characteristics of the ROI.

Figure 4A:
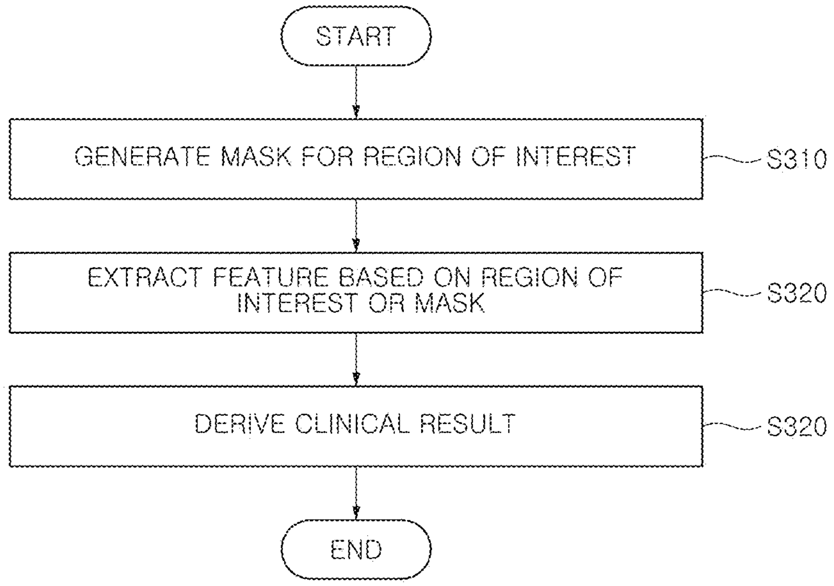

According to various exemplary embodiments of the present disclosure, referring to FIG. 4A, a mask for the ROI may be generated within the filtered medical image (S410), features may be extracted based on the ROI or the mask (S420), and clinical results may be derived based on the extracted features (S430).

In this case, in the step (S420) of extracting the feature, the handcrafted feature of at least one of the morphological features, the texture features, and the pixel histogram-based features may be extracted based on the ROI or the mask.

According to the feature of the present disclosure, in the step (S420) of extracting the feature, the mask may be overlaid on the filtered medical image, and the feature extraction for the overlaid medical image may be performed.

According to the feature of the present disclosure, in the step (S420) of extracting the feature, the discretization of grayscales is performed based on the pixel intensity of the ROI, the radiomics features and the statistical features for the ROI may be extracted based on the discretization result.

Figure 4B:
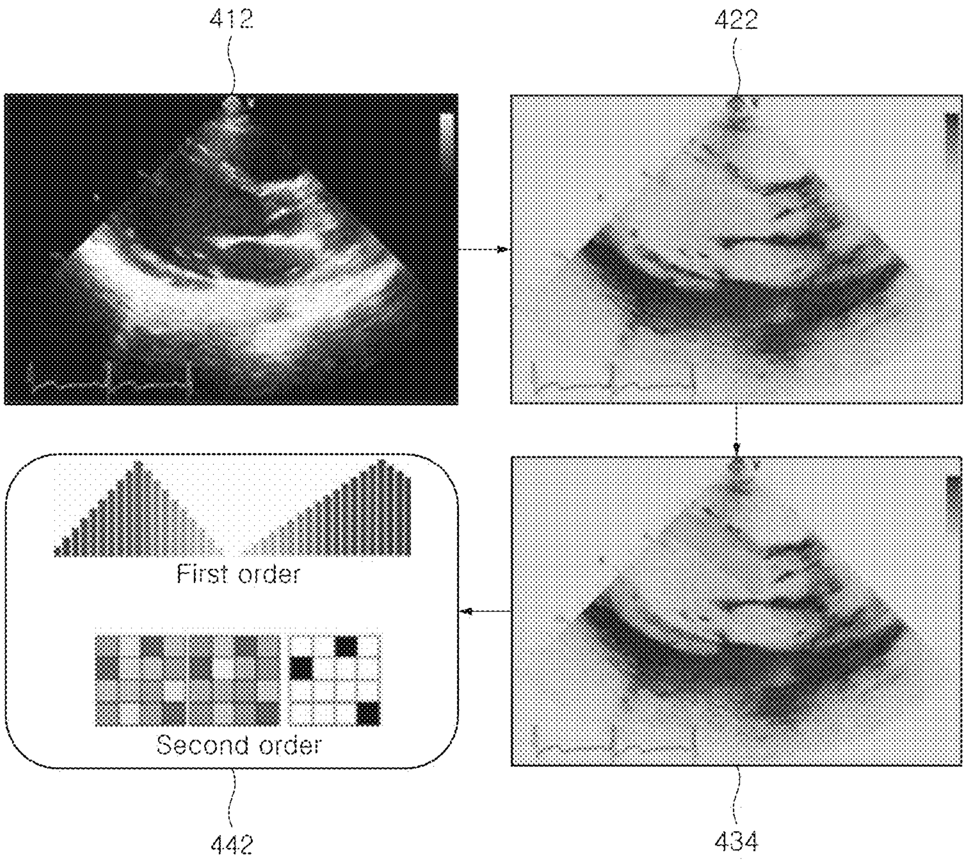

More specifically, referring to FIG. 4B, when the harmonization is performed on a medical image 412, the predictive model is used in the step (S420) of extracting the features to determine the ROI for the harmonized image 422 and extract the mask. Then, the handcrafted features based on the radiomics features and the statistical features are extracted (see 442).

Returning to FIG. 4A, the clinical results may be derived optionally based on the handcrafted features (S430).

However, it is not limited thereto, and the analysis on whether a target disease occurs, prognosis of diseases, etc., may be performed based on the harmonized images.

In various exemplary embodiments of the present disclosure, the derivation of the clinical results may be performed by a classification model based on the handcrafted features or the harmonized medical images.

Therefore, the harmonization method according to various exemplary embodiments of the present disclosure may reduce variability between the medical images acquired from different devices and environments, and generate the harmonized images that maintain consistent features, thereby enabling the accurate disease diagnosis and prognosis prediction. In addition, such harmonized images may be effectively utilized in the machine learning and artificial intelligence-based analysis, thereby contributing to increasing the reliability and reproducibility of medical image analysis.

Evaluation: Evaluation of Predictive Model

Hereinafter, with reference to FIGS. 5A and 5B, 6A and 6B, 7A and 7B, and 8A and 8B, the evaluation results of the predictive model applied to various exemplary embodiments of the present disclosure are described.

In this evaluation, as a model for color-based image processing and analysis, a predictive model (color) based on ConvNeXtV2, which is optimized for effectively extracting color information from various medical image data and performing harmonization, and a predictive model (ultrasound) based on ConvNeXtV2, which is optimized for diagnosing and predicting the prognosis of heart disease by optimizing specific feature extraction and analysis from ultrasound data, were used.

Figure 5A:
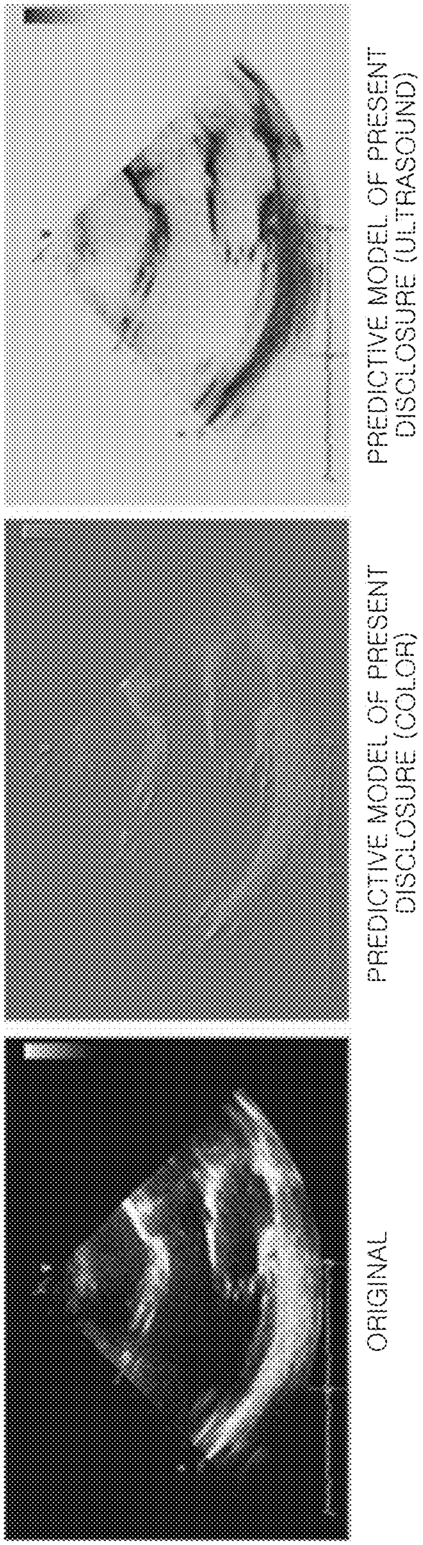
Figure 5B:

First, referring to FIGS. 5A and 5B, the harmonization results based on the convolutional filter are shown by comparing echocardiographic images captured by equipment of two manufacturers (GE in the case of FIG. 5A and Philips in the case of FIG. 5B). More specifically, it appears that the image data acquired from different equipment is consistently converted by the predictive model (ultrasound) used in various exemplary embodiments of the present disclosure.

This may mean that the harmonization based on the predictive model used in various exemplary embodiments of the present disclosure may contribute to increasing the reliability of analysis and diagnosis.

Figure 6A:
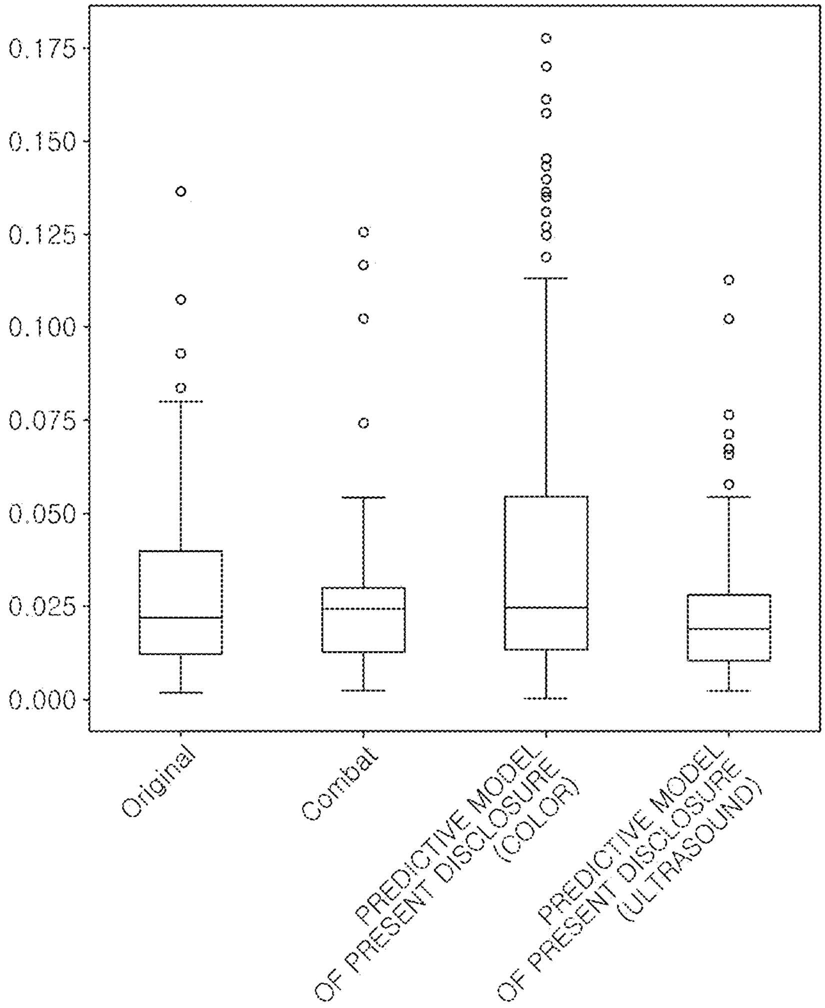

Next, referring to FIGS. 6A and 6B, the harmonization results of the original image, the conventional harmonization method ComBat, and the ultrasound images of two predictive models according to various exemplary embodiments of the present disclosure are compared and illustrated using a box plot based on Jensen-Shannon Divergence (JSD).

More specifically, the JSD is a statistical index that measures similarity between two probability distributions, and may mean that the lower the value, the more similar the two distributions are and mean that when the JSD value is high, the deviation between different data is large and when the JSD value is low, the consistency is high.

In this case, in the case of the predictive model (ultrasound), the JSD value is shown to be the smallest compared to the original data and Combat, which may mean that the variability between the ultrasound image data is effectively reduced.

Figure 7A:
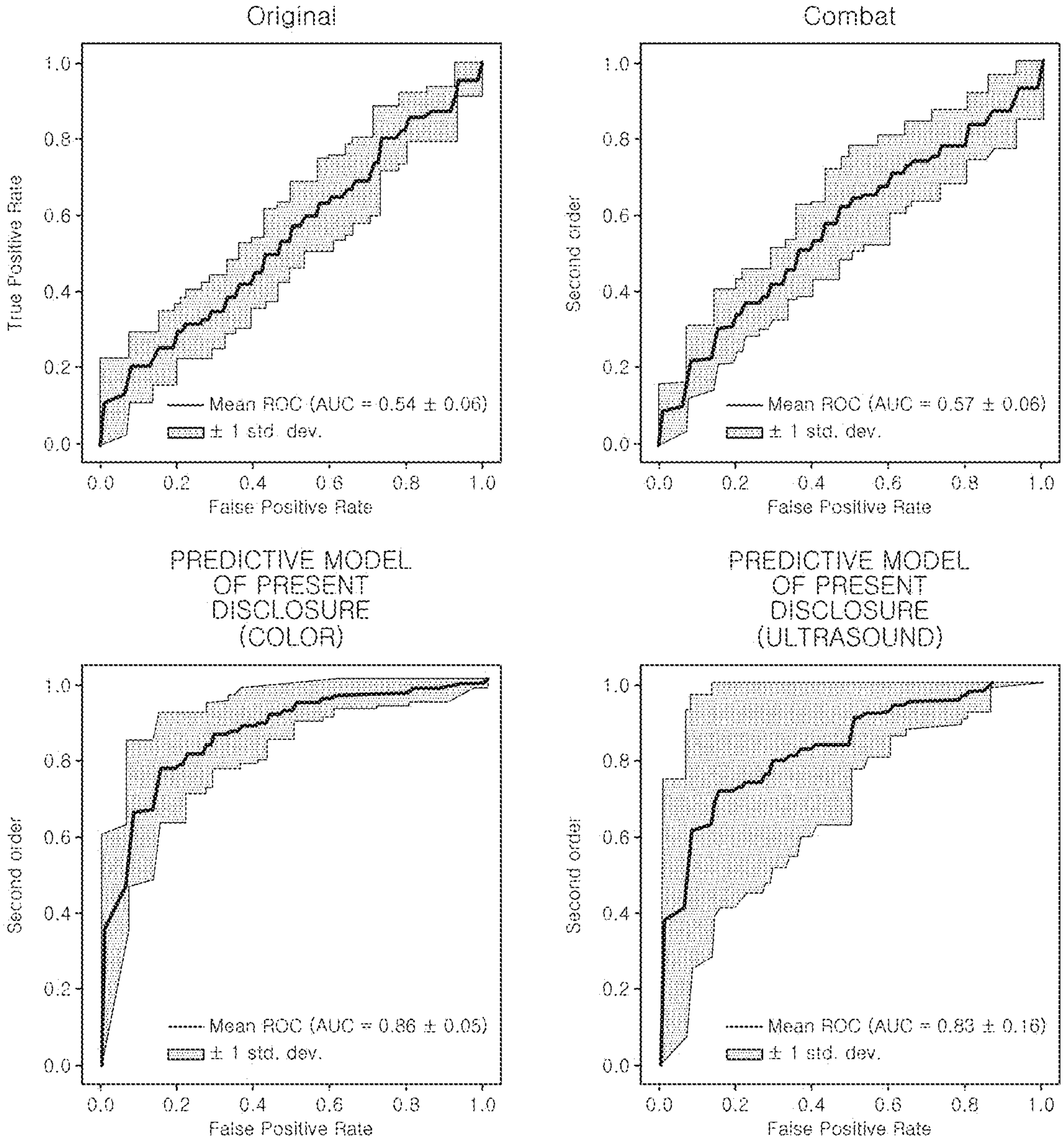

Next, referring to FIGS. 7A and 7B, in classifying the heart diseases of Hypertensive Heart Disease (HDD) and Hypertrophic Cardiomyopathy (HCMP), the evaluation results based on the original image, the conventional harmonization method ComBat, and the two predictive models according to various exemplary embodiments of the present disclosure are compared and illustrated.

More specifically, when the predictive model (color) and the predictive model (ultrasound) are applied, an ROC curve is shown to have a more improved AUC value than the ComBat.

This may mean that the predictive model (color) and the predictive model (ultrasound) may effectively analyze and extract the features of Left Ventricular Hypertrophy (LVH) for the cardiac ultrasound image by using the harmonized cardiac ultrasound image for disease classification.

Figure 8A:
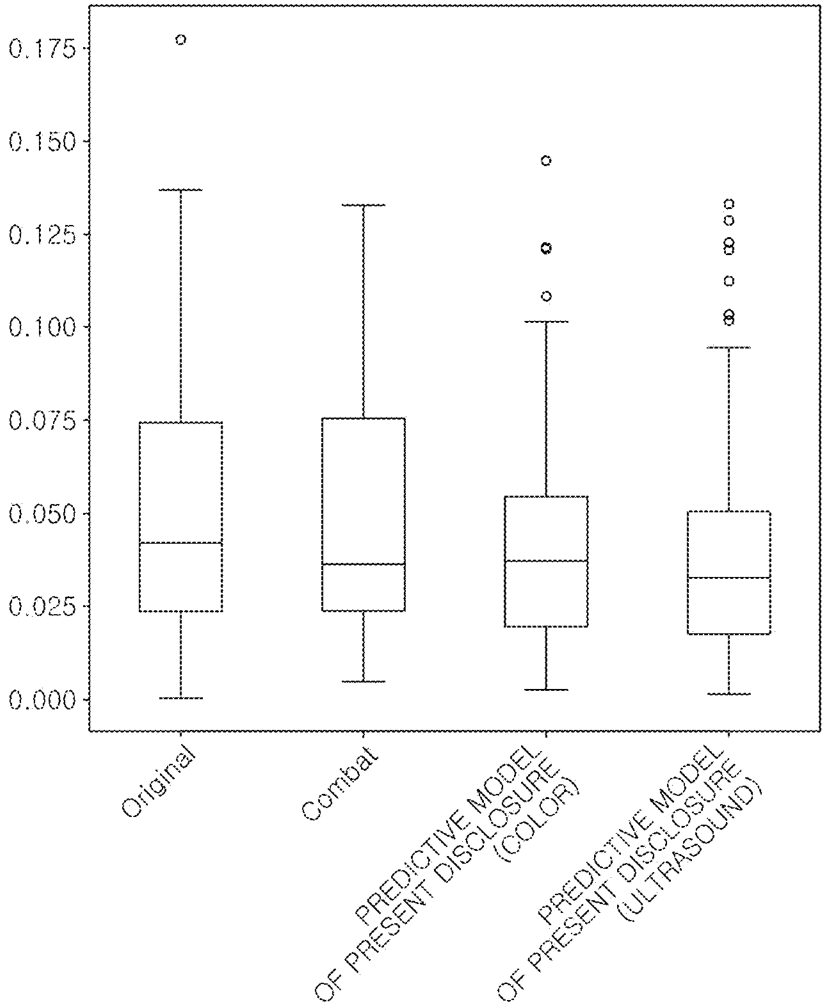

Next, referring to FIGS. 8A and 8B, the harmonization results of the original image, the conventional harmonization method ComBat, and the MRI images of the two predictive models (predictive model (color) and predictive model (MRI)) according to various exemplary embodiments of the present disclosure are compared and illustrated using the box plot based on Jensen-Shannon Divergence (JSD).

More specifically, both the predictive model (color) and the predictive model (MRI) are shown to effectively lower the level of the JSD.

In particular, the predictive model (MRI) trained with the unique features of the MRI images shows that the JSD value is the lowest compared to the original data and the Combat, which may mean that the variability between the MRI image data is effectively reduced.

That is, the present disclosure provides a new system for harmonizing medical images to increase the consistency of data through standardization and harmonization of various medical image data. In particular, the present disclosure may establish a standard for applying the same analysis and diagnosis criteria by reducing a deviation between medical images collected from different manufacturers or capturing environments.

As a result, according to the present disclosure, it is possible to minimize statistical differences between data and derive highly reliable results in clinical diagnosis and research.

In particular, according to the present disclosure, it is possible to support the reliability and reproducibility of handcrafted features through harmonization of medical images through a convolutional filter.

Although the exemplary embodiments of the present disclosure have been described in more detail with reference to the accompanying drawings, the present disclosure is not necessarily limited to these exemplary embodiments, but may be variously modified without departing from the scope and spirit of the present disclosure. Accordingly, the exemplary embodiments disclosed in the present disclosure and the accompanying drawings are used not to limit but to describe the spirit of the present disclosure. The scope of the present disclosure is not limited only to the exemplary embodiments and the accompanying drawings. Therefore, it is to be understood that the exemplary embodiments described above are illustrative rather than being restrictive in all aspects. The scope of the present disclosure should be interpreted by the following claims, and it should be interpreted that all spirits equivalent to the following claims fall within the scope of the present disclosure.

What is claimed is:

1. A method for standardizing a medical image implemented by a processor, the method comprising:

receiving the medical image for an object;

standardizing the received medical image to acquire a filtered medical image by using a convolutional filter based on a predictive model trained to output a reconstructed image using the medical image as input;

generating, using the predictive model, a mask for a region of interest (ROI) in the filtered medical image; and extracting, from the filtered medical image, features based on the region of interest or the mask, wherein the convolutional filter corresponds to a first convolutional layer of the predictive model, wherein the predictive model includes an artificial neural network model based on a masked autoencoder configured to perform self-supervised learning of unique features of the medical image, and wherein the self-supervised learning is performed using unlabeled medical-image data to learn patterns, structural characteristics, or latent representations of the medical image.

2. The method according to claim 1, wherein the extracting of the features includes:

overlaying the mask on the filtered medical image to acquire an overlaid medical image; and extracting features for the overlaid medical image.

3. The method according to claim 1, wherein the extracting of the features includes:

performing discretization of a grayscale based on pixel intensity of the region of interest; and extracting radiomics features and statistical features for the region of interest based on the discretization result.

4. The method according to claim 1, wherein the extracting of the features includes extracting handcrafted features of at least one of morphological features, texture features, and pixel histogram-based features based on the region of interest or the mask.

5. The method according to claim 1, further comprising:

predicting, based on the extracted features, whether a target disease occurs.

6. The method according to claim 1, wherein the first convolutional layer is configured to perform a filtering function of reducing noise of the input medical image by training a feature map divided into patch units for the input medical image.

7. The method according to claim 1, wherein the medical image is at least one of an ultrasound image, an X-ray image, a computed tomography (CT) image, a magnetic resonance imaging (MRI) image, and an endoscopic image.

8. The method according to claim 1, wherein the medical image is a cardiac ultrasound image.

9. A device for standardizing medical images, the device comprising:

a receiver configured to receive a medical image for an object; and a processor functionally connected to the receiver and configured to perform standardization of the received medical image to acquire a filtered medical image by using a convolutional filter based on a predictive model trained to output a reconstructed image using the medical image as input, generate, using the predictive model, a mask for a region of interest in the filtered medical image, and extract, from the filtered medical image, features based on the region of interest or the mask, wherein the convolutional filter corresponds to a first convolution layer of the predictive model, wherein the predictive model includes an artificial neural network model based on a masked autoencoder configured to perform self-supervised learning of unique features of the medical image, and wherein the self-supervised learning is performed using unlabeled medical-image data to learn patterns, structural characteristics, or latent representations of the medical image.

10. The device according to claim 9, wherein the processor is further configured to overlay the mask on the filtered medical image to acquire an overlaid medical image and extract features for the overlaid medical image.

11. The device according to claim 9, wherein the processor is further configured to perform discretization of a grayscale based on pixel intensity of the region of interest, and extract radiomics features and statistical features for the region of interest based on the discretization result.

12. The device according to claim 9, wherein the processor is further configured to extract handcrafted features of at least one of morphological features, texture features, and pixel histogram-based features based on the region of interest or the mask.

13. The device according to claim 9, wherein the processor is further configured to predict whether a target disease occurs based on the extracted features.

14. A device for standardizing medical images, the device comprising:

a receiver configured to receive a medical image for an object; and a processor functionally connected to the receiver and configured to perform standardization of the received medical image to acquire a filtered medical image by using a convolutional filter based on a predictive model trained to output a reconstructed image using the medical image as input, generate, using the predictive model, a mask for a region of interest in the filtered medical image, and extract, from the filtered medical image, features based on the region of interest or the mask, wherein the convolutional filter corresponds to a first convolution layer of the predictive model, wherein the predictive model includes an artificial neural network model based on a masked autoencoder configured to perform self-supervised learning on unique features of the medical image, and wherein the self-supervised learning is performed using unlabeled medical-image data to learn patterns, structural characteristics, or latent representations of the medical image.

15. The device according to claim 9, wherein the first convolutional layer is configured to perform a filtering function of reducing noise of the input medical image by training a feature map divided into patch units for the input medical image.

16. The device according to claim 9, wherein the medical image is at least one of an ultrasound image, an X-ray image, a CT image, an MRI image, and an endoscopic image.

17. The device according to claim 9, wherein the medical image is a cardiac ultrasound image.

* * * * *